(12) United States Patent  (10) Patent No.: US 8,097,210 B2
Ruan  (45) Date of Patent: Jan. 17, 2012

(54) DISPOSABLE TEST SENSOR CARTRIDGE

(75) Inventor: Tieming Ruan, Franklin Lakes, NJ (US)

(73) Assignee: Bayer HealthCare LLC, New York, NY (US)

( * ) Notice: Subject to any disclaimer, the term of this patent is extended or adjusted under 35 U.S.C. 154(b) by 1064 days.

(21) Appl. No.: 11/792,602

(22) PCT Filed: Dec. 16, 2005

(86) PCT No.: PCT/US2005/045760
§ 371 (c)(1),
(2), (4) Date: Nov. 8, 2007

(87) PCT Pub. No.: WO2006/066123
PCT Pub. Date: Jun. 22, 2006

(65) Prior Publication Data
US 2008/0181818 A1     Jul. 31, 2008

Related U.S. Application Data

(60) Provisional application No. 60/637,184, filed on Dec. 17, 2004.

(51) Int. Cl.
*G01N 33/00* (2006.01)

(52) U.S. Cl. ......... 422/63; 422/68.1; 422/400; 422/547; 221/135; 221/277; 221/210; 221/203; 221/231

(58) Field of Classification Search .................. 422/68.1, 422/63; 221/1, 277, 135, 203
See application file for complete search history.

(56) References Cited

U.S. PATENT DOCUMENTS

| 6,534,017 | B1  | 3/2003  | Buttwein et al. |
| 6,908,008 | B2* | 6/2005  | Pugh ............................ 221/135 |
| 7,138,089 | B2* | 11/2006 | Aitken et al. ............. 422/82.01 |
| 7,552,843 | B2* | 6/2009  | Kuriger et al. ................ 221/228 |
| 2002/0057993 | A1 | 5/2002 | Maisey et al. |
| 2002/0076349 | A1 | 6/2002 | Aitken et al. |

(Continued)

FOREIGN PATENT DOCUMENTS

| EP | 0 742 436 A | 11/1996 |
| EP | 1 321 769 A | 6/2003 |

OTHER PUBLICATIONS

Written Opinion of the International Searching Authority corresponding to co-pending International Patent Application No. PCT/US2005/045760, European Patent Office, dated Mar. 31, 2006, 7 pages.

(Continued)

*Primary Examiner* — Sally Sakelaris
(74) *Attorney, Agent, or Firm* — Nixon Peabody LLP

(57) ABSTRACT

This invention relates to a test sensor cartridge assembly that dispenses test sensors individually while shortening the distance of the lateral movement required to eject the sensor. A stationary gear rack is affixed to a surface with a moveable gear rack positioned parallel to the stationary gear rack. The moveable gear rack is adapted to engage the test sensor. A gear is positioned between and contacts the stationary gear rack and the moveable gear rack. The lateral movement of the gear in a first direction generates rotational movement by the gear. Both the lateral and rotational movement move the moveable gear rack laterally in the first direction. The lateral movement of the gear rack in the first direction ejects a test sensor from a test sensor cartridge.

20 Claims, 8 Drawing Sheets

U.S. PATENT DOCUMENTS

| | | |
|---|---|---|
| 2002/0188224 A1 | 12/2002 | Roe et al. |
| 2003/0089730 A1 | 5/2003 | May et al. |
| 2003/0191415 A1 | 10/2003 | Moerman et al. |
| 2003/0223906 A1 | 12/2003 | McAllister et al. |
| 2004/0009100 A1 | 1/2004 | Simons et al. |
| 2008/0181818 A1* | 7/2008 | Ruan .......................... 422/68.1 |

OTHER PUBLICATIONS

International Search Report corresponding to co-pending International Patent Application No. PCT/US2005/045760, European Patent Office, dated Mar. 31, 2006, 5 pages.

* cited by examiner

DISPOSABLE TEST SENSOR CARTRIDGE

CROSS-REFERENCE TO RELATED APPLICATION

This application is a U.S. national phase of International Application No. PCT/US2005/045760, filed Dec. 16, 2005, which claims the benefit of priority of U.S. Provisional Application No. 60/637,184, filed on Dec. 17, 2004, which is incorporated by reference in its entirety.

FIELD OF THE INVENTION

The present invention relates generally to a device and method for dispensing a test sensor. Specifically, the invention is directed to a device and method for dispensing test sensors, one at a time, while shortening the distance of the sliding movement required to dispense a test sensor.

BACKGROUND OF THE INVENTION

Today, test-sensor cartridges are commonly used to individually dispense test sensors. For example, test sensor cartridges may be used in, for example, glucose meters to dispense test sensors for use with the meter. The cartridges are used to store multiple test sensors and assist in keeping the sensors sterile and clean until they are required for use. Typically, the cartridge contains some type of pushing mechanism that ejects each test sensor. In some devices, a slider is used to actuate the pushing mechanism.

Typically, it is necessary for the slider to be moved a distance equal to the distance the test sensor must move to eject the sensor, thus, making it difficult for some users to eject the sensor. For example, people with small hands, such as children, may encounter difficulties dispensing test sensors from typical cartridges.

Thus, there exists a need for a test sensor cartridge that addresses these issues.

SUMMARY OF THE INVENTION

A test sensor ejection mechanism for ejecting a test sensor from a test sensor cartridge is disclosed according to several embodiments of the present invention. In the first embodiment, the test sensor ejection mechanism includes a stationary gear rack, a moveable gear rack, and a gear. The stationary gear rack is affixed to a surface. The moveable gear rack is situated generally parallel to the stationary gear rack and is adapted to engage a test sensor. The gear is positioned between and contacts the stationary gear rack and the moveable gear rack. The lateral movement of the gear in a first direction generates rotational movement by the gear. Both the lateral and rotational movement move the moveable gear rack laterally in the first direction. The lateral movement of the moveable gear rack in the first direction ejects the test sensor from the test sensor cartridge.

According to another embodiment, the ejection mechanism comprises a stationary gear rack, a moveable gear rack, a slot, a gear, a gear core piece, and a slider. The stationary gear rack is affixed to a face of the cartridge. The moveable gear rack is situated parallel to the stationary gear rack and has a foot protruding therefrom. The slot is formed on the face of the cartridge and is adapted to allow the foot to extend therethrough and contact a test sensor. The gear is positioned between and contacts the stationary gear rack and the moveable gear rack and has a central aperture formed therein. The gear core piece runs through the central aperture of the gear, and the slider is attached to the gear core piece. The lateral movement of the slider in a first direction moves the gear in the first direction, which generates rotational movement by the gear. Both the lateral and rotational movement move the moveable gear rack in the first direction. The lateral movement of the moveable gear rack in the first direction ejects the test sensor from the test sensor cartridge.

According to another embodiment, the test sensor dispensing device comprises a test sensor cartridge and an ejection mechanism. The test sensor cartridge forms a central compartment and includes a face and an end wall, stacked test sensors, a test sensor retention mechanism, and a test sensor ejection slit. The face and end wall extend from a base to a top cover. The stacked test sensors are located within the central compartment of the cartridge. The test sensor retention mechanism is located within the central compartment of the cartridge and has a retention plate and at least one spring, which is attached to the retention plate on one end and to the end wall of the cartridge on the other end. The test sensor ejection slit is generally parallel to the face of the cartridge and is adapted to allow one of the test sensors to be ejected from the cartridge. The ejection mechanism includes a stationary gear rack, a moveable gear rack, a slot opening, a gear, a gear core piece, and a slider. The stationary gear rack is affixed to the face of the test sensor cartridge. The moveable gear rack is located generally parallel to the stationary gear rack and has a foot extending therefrom. The slot opening is located on the face of the test sensor cartridge and is adapted to allow the foot to extend therethrough and engage one of the test sensors. The gear is positioned between and contacts the stationary gear rack and the moveable gear rack and has a central aperture formed therein. The gear core piece runs through the central aperture of the gear and allows the gear to rotate thereon. The slider is attached to the gear core piece. The lateral movement of the slider in a first direction moves the gear in the first direction, which generates rotational movement by the gear. Both the lateral and rotational movement move the moveable gear rack laterally in the first direction. The lateral movement of the moveable gear rack in the first direction partially ejects the test sensor from the test sensor cartridge through the ejection slit.

In another embodiment, a meter is adapted to dispense test sensors. The meter includes a read-head, a display, a button set, and an ejection mechanism. The read-head is adapted to determine an analyte concentration from a fluid sample located on a dispensed test sensor. The display displays information to a user of the meter. The button set allows a user to interact with the meter. The ejection mechanism includes a stationary rack, a moveable gear rack, and a gear. The stationary gear rack is affixed to a surface. The moveable gear rack is situated generally parallel to the stationary gear rack and is adapted to engage the test sensor. The gear is positioned between and contacts the stationary gear rack and the moveable gear rack. The lateral movement of the gear rack in a first direction generates rotational movement by the gear. Both the lateral and rotational movement move the moveable gear rack laterally in the first direction. The lateral movement of the moveable gear rack in the first direction ejects the test sensor from the test sensor cartridge.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 7b is a perspective view of the back of the casing of the ejection mechanism of FIG. 7a.

DESCRIPTION OF ILLUSTRATED EMBODIMENTS

The present invention is directed toward a disposable test sensor cartridge and ejection mechanism for dispensing test sensors. The test sensors (e.g. biosensors) ejected from the cartridge may be used in assays for determining the analyte concentration in a fluid sample such as blood or body fluids. Some examples of the types of analytes that may be collected and analyzed include glucose, lipid profiles (e.g., cholesterol, triglycerides, LDL, and HDL), microalbumin, hemoglobin A1C, fructose, lactate, or bilirubin. The quantitative determination of analytes in body fluids is of great importance in the diagnoses and maintenance of certain physiological abnormalities. In particular, determining glucose in body fluids is important to diabetic individuals who must frequently check the glucose level in their body fluids to regulate the glucose intake in their diets. Each test requires that a new test sensor be used, and thus, a number of test strips may be used in a single day. Cartridges that contain a number of test sensors are used to allow users to carry multiple strips around within a single object. These cartridges may also be incorporated directly into a meter or similar device. The blood or body fluid sample may then be analyzed with the meter or similar device to determine the concentration of the analyte being examined.

Figure 1:
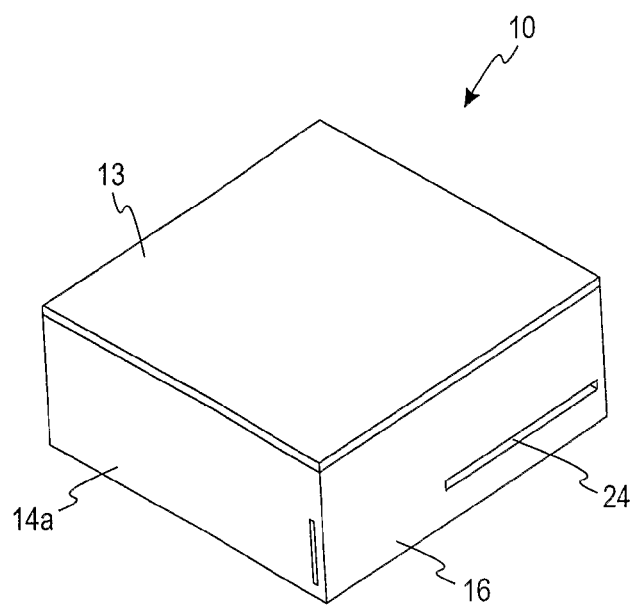
FIG. 1 is a perspective view of a test sensor cartridge according to one embodiment of the present invention.
Figure 2:
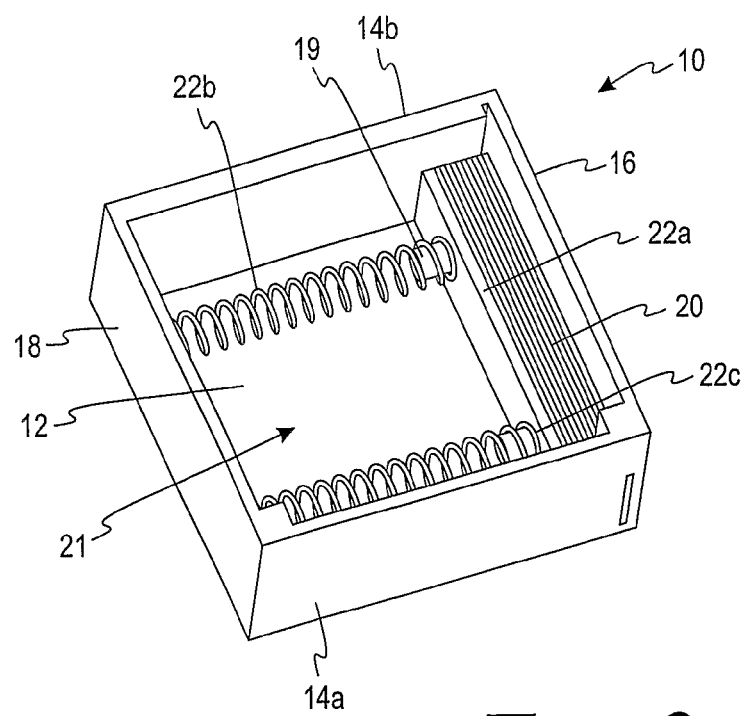
FIG. 2 is a perspective internal view of the cartridge illustrated in FIG. 1.

Turning now to the drawings and initially to FIGS. 1-2, a test sensor cartridge 10 is shown according to one embodiment of the present invention. The test sensor cartridge 10 includes a base 12, a top cover 13, and two opposing side walls 14a and 14b that extend from the base 12 and support the top cover 13. The cartridge 10 also has a face 16 and an end 18 that extend from the base 12 and support the top cover 13. The cartridge 10 is adapted to contain a plurality of test sensors 20 within a central cavity 21 created by the sidewalls 14a-b, the face 16, and the end 18, and between the base 12 and the cover 13.

The cartridge 10 further includes a test sensor retention mechanism 22 that is located within the central cavity 21. The test sensor retention mechanism 22 comprises a retention plate 22a and a plurality of springs 22b,c. The test sensors 20 are stacked between the face 16 of the cartridge 10 and the retention plate 22a. The retention mechanism 22 is used to ensure that the test sensors 20 remain in contact with each other and are flush with an interior surface of the face 16. The test sensor retention mechanism 22 drives the test sensors 20 toward the interior surface of the face 16. The springs 22b,c are positioned between the retention plate 22a and the end 18 and are attached to both the retention plate 22a and the end 18. For example, the springs 22b,c may be attached by extending a protrusion 19 from the end 18 and another from the retention plate 22a into a central aperture of the springs 22b,c. It is contemplated that the springs 22b,c may be attached by other methods. The springs 22b,c provide a force on the retention plate 22a in the direction of the face 16. Though the illustrated embodiment shows two springs 22b,c being used to apply a force to the retention plate 22a, it should be noted that a different number of springs may be used in the present invention, such as one spring.

Figure 3:
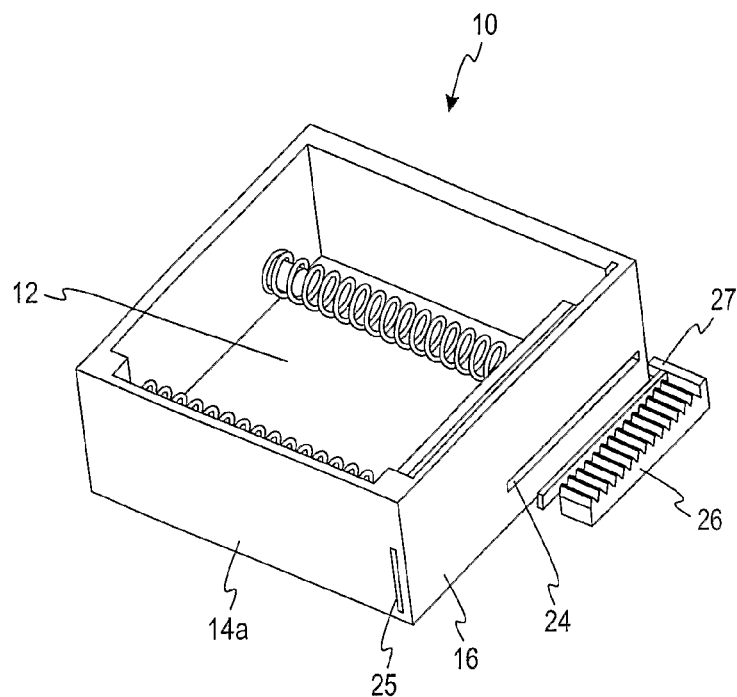
FIG. 3 is a perspective internal view of the test sensor cartridge of FIG. 2 with the moveable gear rack shown.

Referring also to FIG. 3, the face 16 of the cartridge 10 forms a slot 24 running generally parallel to the base 12. The slot 24 is adapted to allow an ejection mechanism 11 (FIG. 5a) to be inserted through the slot 24. Initially, the slot 24 may be sealed, for example, by attaching foil to the face 16 of the cartridge 10. Sealing the slot protects the stacked test sensors from humidity. The side wall 14a has an ejection slit 25 running perpendicular to the base 12 sufficient to allow the test sensors to be ejected from the cartridge 10 one at a time.

Figure 4:
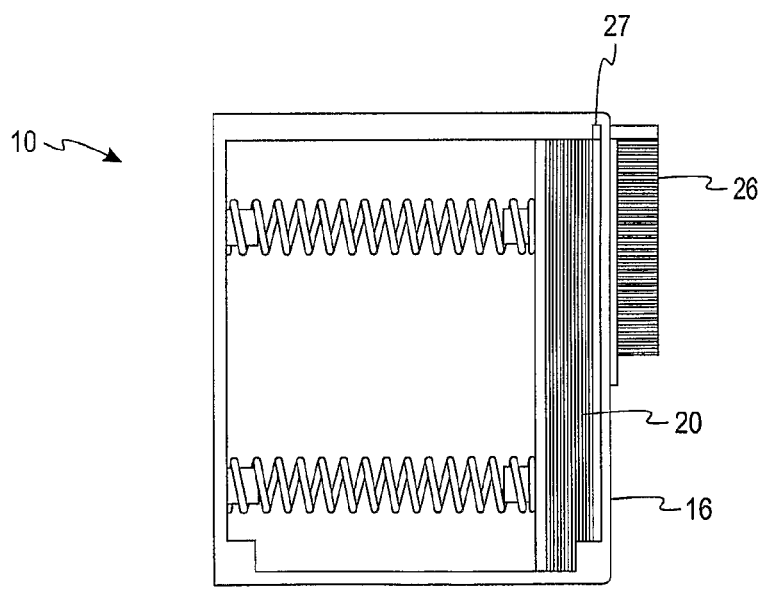
FIG. 4 is a top view of the cartridge of FIG. 3 showing the moveable gear rack inserted into the test sensor cartridge of FIG. 1.

FIG. 3 also illustrates a moveable gear rack 26 positioned near the slot 24 of the cartridge 10. The moveable gear rack 26 includes a foot 27 protruding therefrom. The foot 27 is designed to insert through the slot 24 behind an end of the test sensor that is flush with the interior surface of the face 16, as shown in FIG. 4. The foot 27 is designed to contact only a single test sensor 20 closest to the face 16 of the test sensor cartridge 10. The moveable gear rack 26 is adapted to removably attach to the cartridge 10 when the foot 27 is inserted through the slot 24. The foot 27 can reciprocally move from a standby position to an ejection position. It is contemplated that other types of ejection schemes or devices may be used in place of the foot 27 described herein.

Figure 5A:
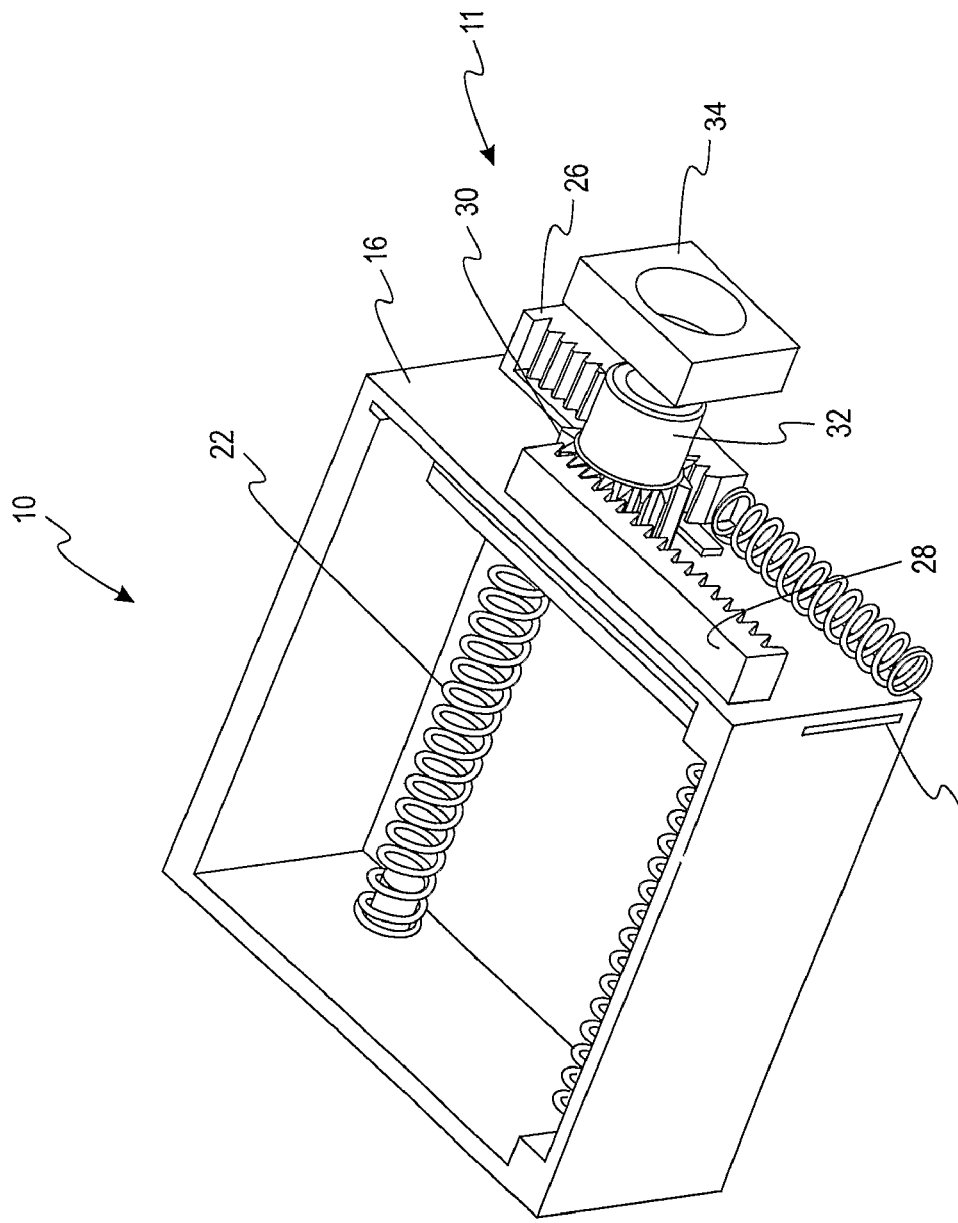
FIG. 5a is a schematic view of an ejection mechanism attached to the test sensor cartridge of FIG. 2 with the ejection mechanism being in a standby position.
Figure 5B:
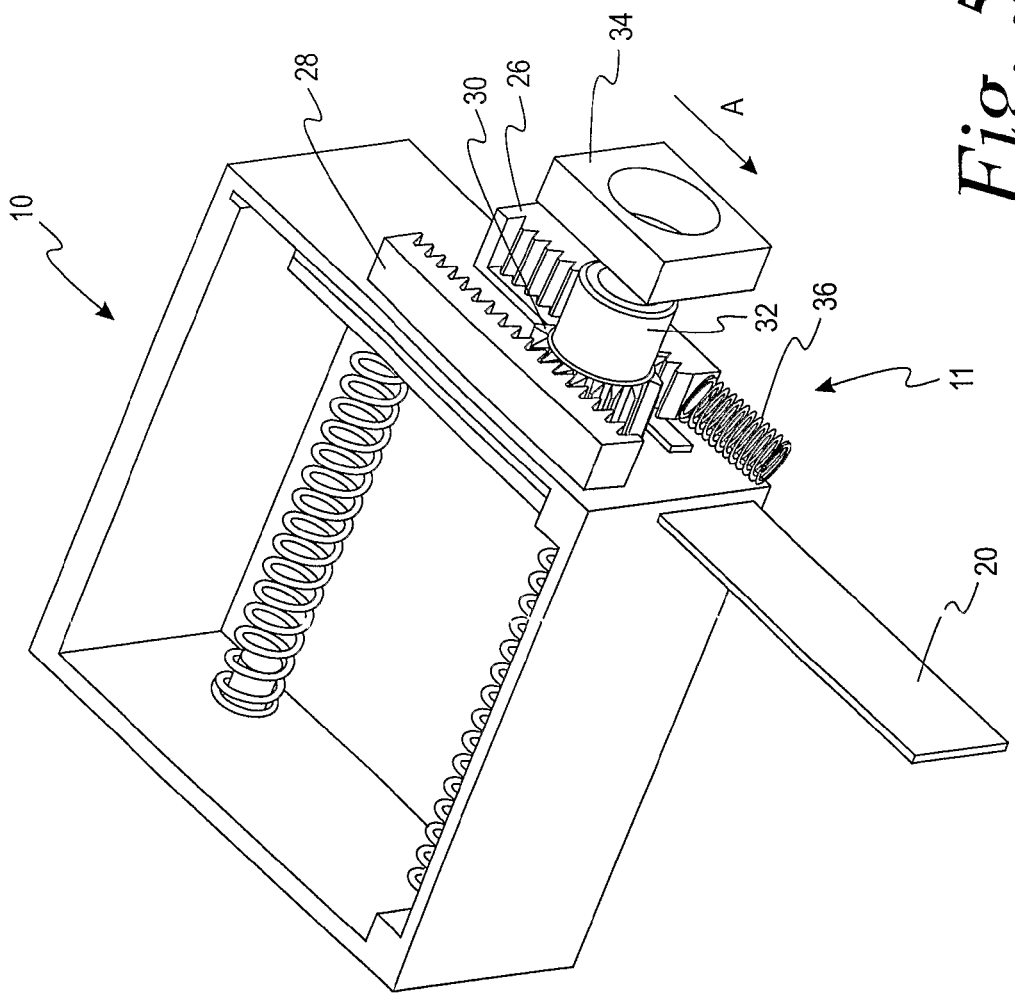
FIG. 5b is a schematic view of the ejection mechanism and cartridge of FIG. 5a with the ejection mechanism being in an ejection position.

FIGS. 5a-b illustrate the cartridge 10 of FIGS. 1-2 with a stationary gear rack 28 attached to the face 16 of the cartridge 10. The moveable gear rack 26 has been removably attached to the cartridge 10 by inserting the foot 27 through the slot 24. The stationary gear rack 28 is fixed on the face 16 of the cartridge 10, while the moveable gear rack 26 is positioned to cover the slot 24. A gear 30 is located between the stationary gear rack 28 and the moveable gear rack 26. The gear 30 contacts both the stationary gear rack 28 and the moveable gear rack 26. The gear 30, the stationary gear rack 28, and the moveable gear rack 26 all contain teeth. The teeth of the gear 30 are adapted to insert between the teeth of the stationary gear rack 28 and the moveable gear rack 26. The gear 30 has a core piece 32 running through a central aperture (not shown) and a slider 34 that is attached to the core piece 32. The gear 30 is allowed to rotate on the core piece 32 when the user moves the slider 34.

The gear 30 and the racks 26,28 are in a dual-rack and pinion configuration. Thus, as the slider 34 is moved laterally from a standby position (FIG. 5a) to an ejection position (FIG. 5b)—in the direction of arrow A (FIGS. 5a-b)—the gear 30 is also moved laterally and the stationary gear rack 28 causes the gear 30 to rotate in a clockwise direction as well. Both the lateral movement of the gear 30 and the rotation of the gear 30 cause the moveable gear rack 26 to move laterally in the direction of arrow A. For example, when the slider 34 is moved laterally a distance X, the gear 30 is moved X distance laterally as well, which causes the moveable gear rack 26 to move a lateral distance X. Additionally, as the gear 30 is moved laterally, the fixed gear rack 26 causes the gear 30 (i.e., the pinion) to rotate clockwise (in the illustrated embodiment). This rotation further moves the moveable gear rack 26 a distance Y based on the size of the gear 30 and the configuration of the teeth on the gear 30 and the racks 26,28. Thus, lateral movement of the slider 34 an X distance in the direction of arrow A causes the moveable gear rack 26 to travel laterally a distance of X+Y in the direction of arrow A.

As discussed above, the foot 27 of the moveable gear rack is positioned behind the test sensor 20 that is proximate the face 16. Thus, the test sensor 20 laterally moves X+Y distance in the same direction of the slider 34, when the slider 34 is moved X distance. As the moveable gear rack 26 is moved laterally in the direction of arrow A, the test sensor 20 proximate the face 16 of the cartridge is partially ejected through the ejection slit 25 by the foot 27. When the test sensor 20 is removed, the test sensor retention mechanism 22 forces the remaining stack of test sensors 20 towards the face 16 until the next proximate test sensor 20 becomes flush with the face 16.

A spring 36 is situated adjacent to the moveable gear rack 26 nearest the ejection slit 25. When the moveable gear rack 26 is moved toward the ejection slit 25, the spring 36 compresses, such that when the slider 34 is released, the return force of the spring 36 repositions the moveable gear rack 26 to its starting position for ejecting another test sensor 20.

As discussed above, in some embodiments, the slot 24 may be sealed with foil, such as, for example, AL-191-01 foil distributed by Alusuisse Flexible Packaging, Inc. Additionally, the ejection slit 25 may be sealed with foil. In these embodiments, the foot 27 initially punctures the foil sealing of the slot 24 when it is attached to the cartridge 10. The foot 27 then slices the foil sealing the slot 27 as the slider 34 is moved laterally in the direction of arrow A. As the foot 27 moves in the direction of arrow A, a test sensor 20 is dispensed from the cartridge 10. The test sensor 20 that is dispensed first slices the foil sealing the ejection slit 25.

Figure 6:
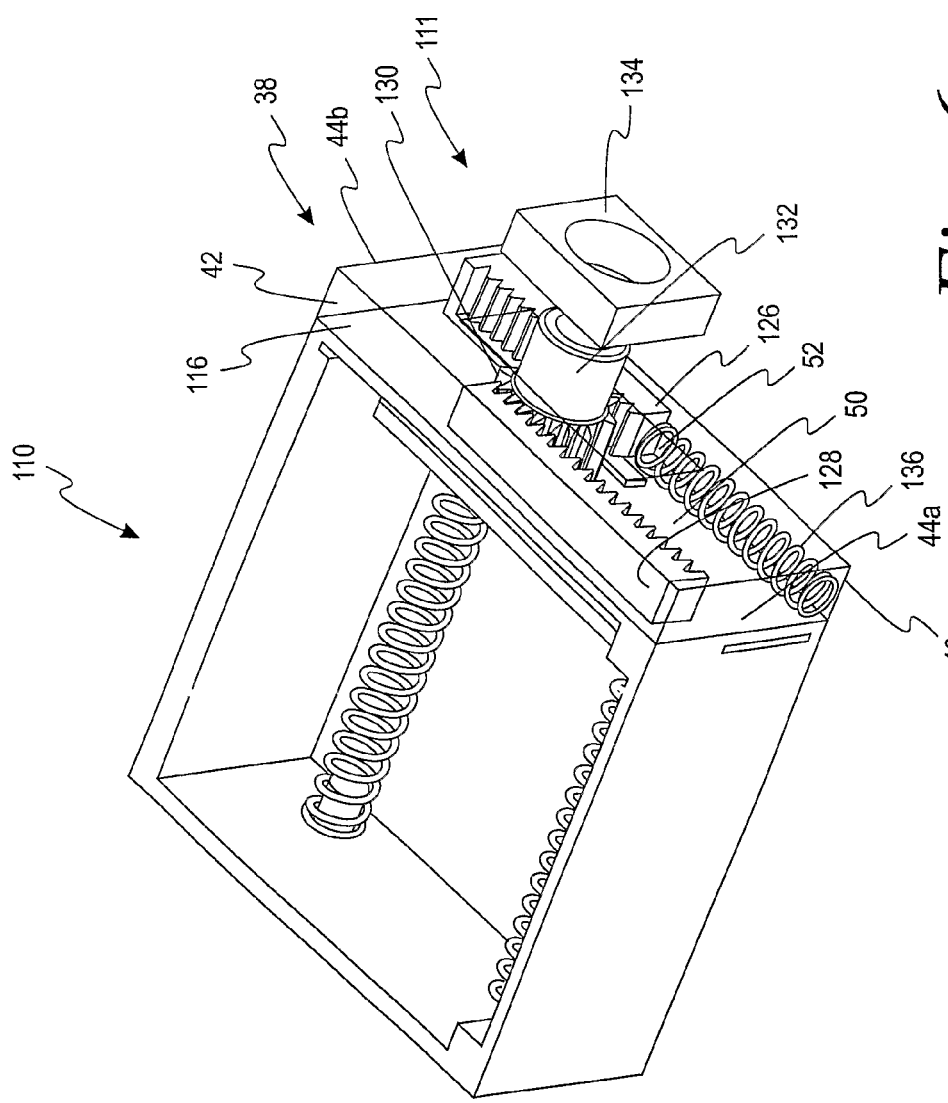
FIG. 6 is a schematic view of an alternative embodiment of the test sensor cartridge and sliding mechanism of FIG. 5, where the ejection mechanism is enclosed by a casing.

Turning now to FIG. 6, an ejection mechanism 111 is illustrated within a casing 38 and attached to a cartridge 110 according to another embodiment of the present invention. The ejection mechanism 111 includes the stationary gear rack 128, a moveable gear rack 126 with a foot on one end, a spring 136, and a gear 130, all partially enclosed within the casing 38. The casing 38 includes a bottom 40, a top 42, and a front 50. The casing 38 also has two sides 44a and 44b extending from the bottom 40 to the top 42. A face 116 of the cartridge 110 serves as a rear wall for the casing 38. The face 116 includes a slot of similar size and dimensions as the slot 24 of FIGS. 1 and 3 through which the foot protrudes. The bottom 40 provides a path on which the moveable gear rack 126 travels. The bottom 40 and front 50 of the casing 38 also hold the moveable gear rack 126 and the spring 136 in place, ensuring that the foot remains positioned in the slot. The front 50 has an opening 52 adapted to allow a core piece 132 to extend therethrough. The slider 134 is located outside of the casing 38 so a user may access it. The opening 52 is adapted to allow the user to move the slider 134 so that a test sensor may be ejected.

Figure 7A:
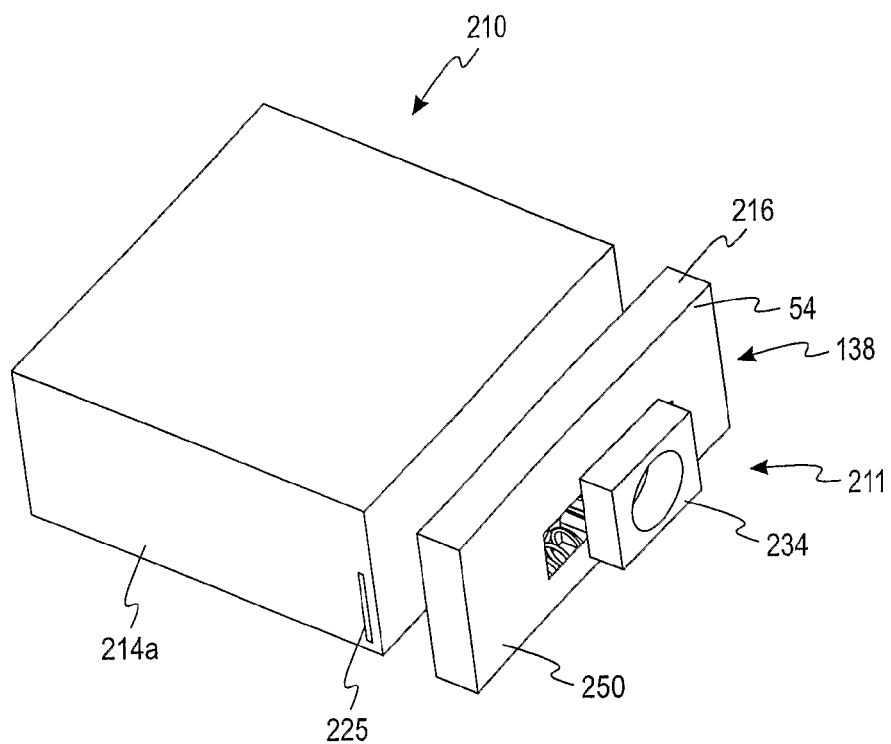
FIG. 7a is a perspective view of the test sensor cartridge and an ejection mechanism that is removably attachable to the test sensor cartridge according to one embodiment of the present invention.
Figure 7B:
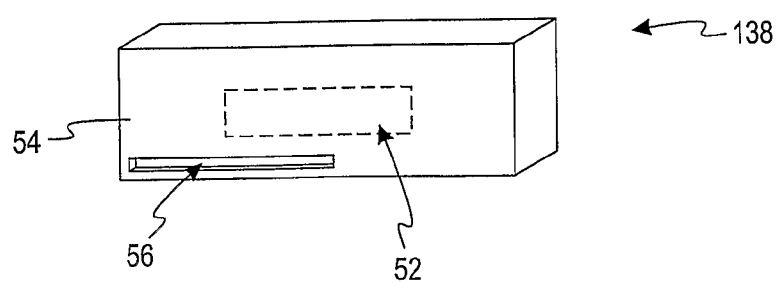

Turning now to FIGS. 7a-b, a removable casing 138 is illustrated according to another embodiment. The removable casing 138 is removably attachable to the cartridge 210. The removable casing 138 is similar to the casing 38 of FIG. 6, except that the removable casing 138 has a back 54 affixed thereto to substantially enclose the ejection mechanism 211. The removable casing 138 includes the same internal features as the casing 38 of FIG. 6. In the illustrated embodiment of FIG. 7a,b, a slot 56 is formed in the back 54 of the removable casing 138. The cartridge 210 has a slot on a face 216 of similar dimensions as the slot 24 formed in the cartridge 10 of FIG. 1. The slot 56 has similar dimensions to the slot 24 formed in the cartridge 10 and is adapted to allow the foot of the moveable gear rack 226 to extend therethrough. When the removable casing 138 is removably attached to the cartridge 210, the slot 56 aligns with the slot on the face 216 of the cartridge 210 such that the foot of the moveable gear rack 226 inserts into the cartridge 210 through the slot. When the foot is so inserted, the ejection mechanism 211 can dispense a test sensor from the cartridge 210.

The back 54 of the removable casing 138 is adapted to removably attach to the face 216 of the cartridge 210. This removable attachment can be achieved through a variety of means including, but not limited to, slot(s) and groove(s) connections, one or more latching mechanisms, an adhesive, etc.

Figure 8:
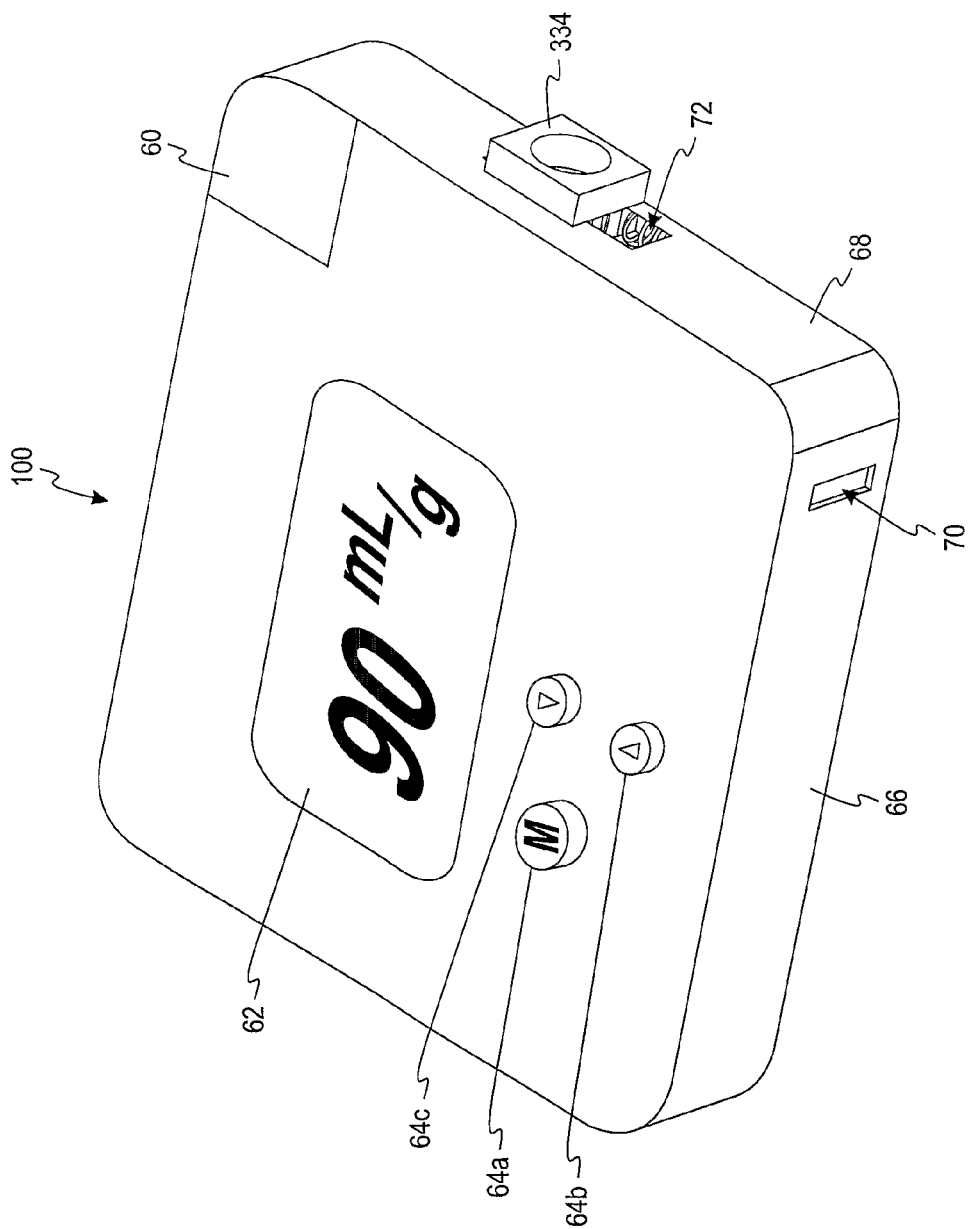
FIG. 8 is a perspective view of a meter to which the ejection mechanism of FIG. 5 is attached internally in one embodiment of the invention.

According to some embodiments of the invention, the cartridge 110 or 210 and the casing 38 or removable casing 138 are adapted to be inserted into a meter 100, as shown in FIG. 8. According to one embodiment, the meter 100 comprises a display 62, a read-head 60, and a button set 64 that includes a plurality of buttons 64a-c. The read-head 60 is adapted to obtain a reading from a fluid sample applied to the test sensor 20 while the button set 64 allows a user to interact with the meter 100. The meter 100 is adapted so that the side wall of the cartridge is proximate to a first surface 66 and a second surface 68 of the meter 100. The first surface 66 contains an test sensor ejection opening 70 that aligns with an ejection slit of the cartridge, such that when a test sensor is ejected through the ejection slit of the cartridge, it is also ejected through the test sensor ejection opening 70. An adjacent second surface 68 includes a slot opening 72 that allows a user to access and move the slider 334. The slot opening 72 is adapted to allow the core piece of the ejection mechanism 111,211 to reciprocally move from a standby position to a testing position. In an alternative embodiment, the ejection mechanism 211 and casing 138 of FIGS. 7a-b are initially enclosed in the meter 100 and the cartridge 210 may be later inserted into the meter 100 so that the face 216 of the cartridge 210 is flush with the back 54 of the casing 138 and the side wall 214a of the cartridge is flush with the first surface 66 of the meter 100. When the cartridge 210 is properly inserted, the ejection slit 225 aligns with the test sensor ejection opening 70 formed in the meter 100.

Figure 9:
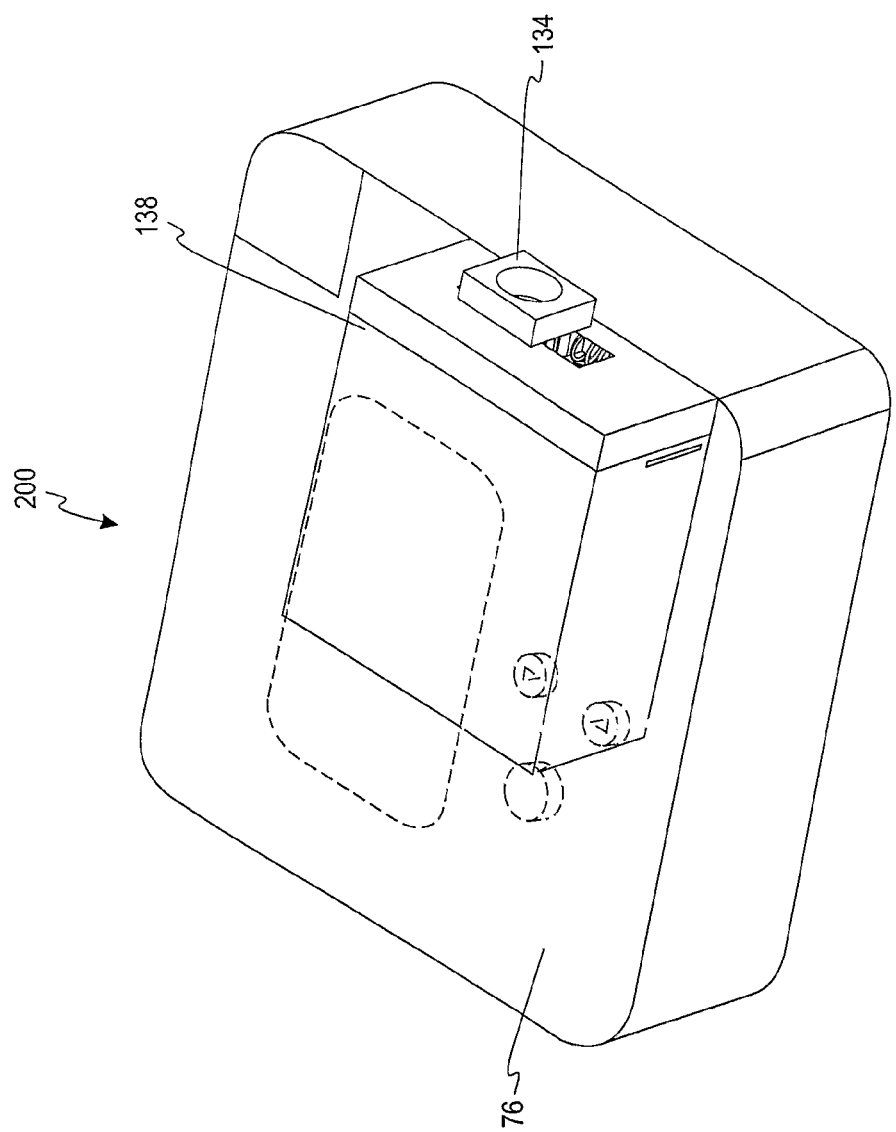
FIG. 9 is a perspective view of the ejection mechanism of FIG. 6 attached externally to the meter of FIG. 8.

Referring now to FIG. 9, the ejection mechanism 111,211 of FIGS. 7a-b is attached to a meter 200, according to one embodiment of the present invention. The ejection mechanism 111,211 is attached to an exterior surface 76 of the meter 200. The back 54 (FIG. 7b) of the casing 138 is adapted to contact the face 216 of the cartridge so that the slot 56 of the casing 138 aligns with the slot on the face 216 of the cartridge 210. In this embodiment, the cartridge 210 remains external to the meter 200 during use.

Alternative Embodiment A

A test sensor ejection mechanism for ejecting a test sensor from a test sensor cartridge, the ejection mechanism comprising:

a stationary gear rack affixed to a surface;

a moveable gear rack situated generally parallel to the stationary gear rack, the moveable gear rack being adapted to engage the test sensor; and a gear positioned between and contacting the stationary gear rack and the moveable gear rack, wherein lateral movement of the gear in a first direction generates rotational movement by the gear, both the lateral and rotational movement moving the moveable gear rack laterally in the first direction, the lateral movement of the moveable gear rack in the first direction ejecting the test sensor from the test sensor cartridge.

Alternative Embodiment B

The test sensor ejection mechanism of embodiment A wherein the lateral distance the moveable gear rack moves is twice the distance the gear moves.

Alternative Embodiment C

The test sensor ejection mechanism of embodiment A further comprising a slider mechanically attached to the gear, wherein movement of the slider in the first direction moves the gear in the first direction.

Alternative Embodiment D

The test sensor ejection mechanism of embodiment A wherein the ejection mechanism is at least partially enclosed by a casing.

Alternative Embodiment E

The test sensor ejection mechanism of embodiment D wherein the casing is adapted to be removably attached to a meter.

Alternative Embodiment F

The test sensor ejection mechanism of embodiment D wherein the casing is adapted to removably attach to the test sensor cartridge.

Alternative Embodiment G

The test sensor ejection mechanism of embodiment A wherein the test sensor is adapted to assist in the determination of an analyte concentration in a fluid sample.

Alternative Embodiment H

The test sensor ejection mechanism of embodiment G wherein the analyte is glucose and the fluid sample is whole blood.

Alternative Embodiment I

A test sensor ejection mechanism, for ejecting a test sensor from a test sensor cartridge, the ejection mechanism comprising:
 a stationary gear rack affixed to a face of the cartridge;
 a moveable gear rack situated parallel to the stationary gear rack, the moveable gear rack having a foot protruding therefrom;
 a slot formed on the face of the cartridge, the slot being adapted to allow the foot to extend therethrough and contact the test sensor;
 a gear positioned between and contacting the stationary gear rack and the moveable gear rack, the gear having a central aperture formed therein;
 a gear core piece running through the central aperture of the gear; and
 a slider attached to the gear core piece,
 wherein lateral movement of the slider in a first direction moves the gear in the first direction, which generates rotational movement by the gear, both the lateral and rotational movement moving the moveable gear rack laterally in the first direction, the lateral movement of the moveable gear rack in the first direction ejecting the test sensor from the test sensor cartridge.

Alternative Embodiment J

The test sensor ejection mechanism of embodiment I wherein the cartridge includes a plurality of test sensors located therein.

Alternative Embodiment K

The test sensor ejection mechanism of embodiment J wherein the cartridge includes a test sensor retention mechanism for putting one of the plurality of test sensors flush with the face of the cartridge.

Alternative Embodiment L

The test sensor ejection mechanism of embodiment K wherein the ejection mechanism and the cartridge are adapted to insert into a meter.

Alternative Embodiment M

The test sensor ejection mechanism of embodiment K wherein the ejection mechanism and the cartridge are adapted to removably attach to a meter.

Alternative Embodiment N

A test sensor dispensing device, comprising:
 a test sensor cartridge forming a central compartment, the cartridge including
  (i) a face and an end wall extending from a base to a top cover,
  (ii) a plurality of stacked test sensors located within the central compartment of the cartridge,
  (iii) a test sensor retention mechanism located within the central compartment of the cartridge, the retention mechanism having a retention plate and at least one spring, the at least one spring being attached to the retention plate on one end and to the end wall of the cartridge on the other end, and
  (iv) a test sensor ejection slit generally parallel to the face of the cartridge, the ejection slit being adapted to allow one of the plurality of test sensors to be ejected from the cartridge; and
 an ejection mechanism including
  (i) a stationary gear rack affixed to the face of the test sensor cartridge,
  (ii) a moveable gear rack located generally parallel to the stationary gear rack, the moveable gear rack having a foot extending therefrom,
  (iii) a slot opening on the face of the test sensor cartridge, the slot opening being adapted to allow the foot to extend therethrough and engage one of the plurality of test sensors, (iv) a gear positioned between and contacting the stationary gear rack and the moveable gear rack, the gear having a central aperture formed therein, (v) a gear core piece running through the central aperture of the gear, the gear core piece allowing the gear to rotate thereon, and (vi) a slider attached to the gear core piece, wherein lateral movement of the slider in a first direction moves the gear in the first direction, which generates rotational movement by the gear, both the lateral and rotational movement moving the moveable gear rack laterally in the first direction, the lateral movement of the moveable gear rack in the first direction partially ejecting the test sensor from the test sensor cartridge through the ejection slit.

Alternative Embodiment O

The test sensor dispensing device of embodiment N wherein the test sensor dispensing device is attached to a meter.

Alternative Embodiment P

The test sensor dispensing device of embodiment N wherein the ejection mechanism is enclosed in a casing, the casing including an opening through which the gear core piece and slider project.

Alternative Embodiment Q

The test sensor dispensing device of embodiment P wherein the face of the test sensor cartridge functions as a rear wall for the casing.

Alternative Embodiment R

The test sensor dispensing device of embodiment N wherein the slot opening is initially sealed with foil.

Alternative Embodiment S

The test sensor dispensing device of embodiment N wherein the ejection slit is initially sealed with foil.

Alternative Embodiment T

A meter adapted to dispense test sensors, the meter comprising:
a read-head adapted to determine an analyte concentration from a fluid sample located on a dispensed test sensor;
a display for displaying information to a user of the meter;
a button set for allowing a user to interact with the meter; and
an ejection mechanism including
(i) a stationary gear rack affixed to a surface,
(ii) a moveable gear rack situated generally parallel to the stationary gear rack, the moveable gear rack adapted to engage the test sensor, and
(iii) a gear positioned between and contacting the stationary gear rack and the moveable gear rack,
wherein lateral movement of the gear in a first direction generates rotational movement by the gear, both the lateral and rotational movement moving the moveable gear rack laterally in the first direction, the lateral movement of the moveable gear rack in the first direction ejecting the test sensor from the test sensor cartridge.

Alternative Embodiment U

The meter of embodiment T wherein the analyte is glucose and the fluid sample is whole blood.

Alternative Embodiment V

The meter of embodiment T wherein the ejection mechanism is attached to an exterior surface of the meter.

Alternative Embodiment W

The meter of embodiment T the meter further comprising an internal cavity adapted to allow a test sensor cartridge to be inserted into the meter, the ejection mechanism being attached within the internal cavity so as to allow the gear to be laterally moved in the first direction from outside the meter.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention claimed is:

1. A test sensor ejection mechanism for ejecting at least one test sensor from a test sensor cartridge, the ejection mechanism comprising:
a casing configured to removably attach to the test sensor cartridge;
a stationary gear rack affixed to a surface within the casing;
a moveable gear rack situated within the casing generally parallel to the stationary gear rack, the moveable gear rack having a foot protruding therefrom, the foot extending out of the casing and configured to be inserted into an opening formed in a wall of the test sensor cartridge such that the foot engages the at least one test sensor; and
a gear positioned between and contacting the stationary gear rack and the moveable gear rack,
wherein lateral movement of the gear in a first direction generates rotational movement by the gear, both the lateral and rotational movement moving the moveable gear rack laterally in the first direction, the lateral movement of the moveable gear rack in the first direction ejecting the at least one test sensor from the test sensor cartridge.

2. The test sensor ejection mechanism of claim 1, wherein the lateral distance the moveable gear rack moves is twice the distance of the gear moves.

3. The test sensor ejection mechanism of claim 1, further comprising a slider mechanically attached to the gear, wherein movement of the slider in the first direction moves the gear in the first direction.

4. The test sensor ejection mechanism of claim 1, wherein the casing is adapted to be removably attached to a meter.

5. The test sensor ejection mechanism of claim 1, wherein the test sensor is adapted to assist in the determination of an analyte concentration in a fluid sample.

6. The test sensor ejection mechanism of claim 5, wherein the analyte is glucose and the fluid sample is whole blood.

7. A test sensor ejection mechanism for ejecting at least one test sensor from a test sensor cartridge, the ejection mechanism comprising:
a stationary gear rack affixed to a face of the cartridge;
a moveable gear rack situated generally parallel to the stationary gear rack, the moveable gear rack having a foot protruding therefrom;

a slot formed in the face of the cartridge, the foot extending through the slot such that the foot engages the at least one test sensor;

a gear positioned between and contacting the stationary gear rack and the moveable gear rack, the gear having a central aperture formed therein;

a gear core piece running through the central aperture of the gear; and a slider attached to the gear core piece, wherein lateral movement of the slider in a first direction moves the gear in the first direction, which generates rotational movement by the gear, both the lateral and rotational movement moving the moveable gear rack laterally in the first direction, the lateral movement of the moveable gear rack in the first direction ejecting the at least one test sensor from the test sensor cartridge.

8. The test sensor ejection mechanism of claim 7, wherein the moveable gear rack is adapted to removably attach to the face of the cartridge.

9. The test sensor ejection mechanism of claim 7, wherein the cartridge includes a plurality of test sensors and a test sensor retention mechanism for putting one of the plurality of test sensors flush with the face of the cartridge.

10. A test sensor dispensing device, comprising:
a test sensor cartridge with a face and an end wall extending from a base to a top cover, the cartridge forming a central compartment, the cartridge including:
a plurality of stacked test sensors located within the central compartment of the cartridge;
a test sensor retention mechanism located within the central compartment of the cartridge, the retention mechanism having a retention plate and at least one spring, the at least one spring engaging the retention plate on one end and the end wall of the cartridge on the other end; and
a test sensor ejection slit generally parallel to the face of the cartridge, the ejection slit being configured to allow at least one of the plurality of test sensors to be ejected from the cartridge; and
an ejection mechanism including:
a stationary gear rack affixed to the face of the test sensor cartridge;
a moveable gear rack generally parallel to the stationary gear rack, the moveable gear rack having a foot extending therefrom;
a slot formed in the face of the test sensor cartridge, the foot extending through the slot such that the foot engages the at least one test sensor;

a gear positioned between and contacting the stationary gear rack and the moveable gear rack, the gear having a central aperture formed therein;

a gear core piece running through the central aperture of the gear, the gear core piece allowing the gear to rotate thereon; and a slider attached to the gear core piece, wherein lateral movement of the slider in a first direction moves the gear in the first direction, which generates rotational movement by the gear, both the lateral and rotational movement moving the moveable gear rack laterally in the first direction, the lateral movement of the moveable gear rack in the first direction partially ejecting the test sensor from the test sensor cartridge through the ejection slit.

11. The test sensor dispensing device of claim 10, wherein the test sensor dispensing device is attached to a meter.

12. The test sensor dispensing device of claim 10, wherein the ejection mechanism is enclosed in a casing, the casing including an opening through which the gear core piece and slider project.

13. The test sensor dispensing device of claim 12, wherein the face of the test sensor cartridge functions as a rear wall for the casing.

14. The test sensor dispensing device of claim 10, wherein the slot is initially sealed with foil.

15. The test sensor dispensing device of claim 10, wherein the ejection slit is initially sealed with foil.

16. The test sensor ejection mechanism of claim 1, further comprising a biasing member disposed within the casing, the biasing member being engaged with and biasing the moveable gear rack in a second direction opposite the first direction.

17. The test sensor ejection mechanism of claim 1, wherein the casing defines an elongated slot, the foot extending through the elongated slot and out of the casing.

18. The test sensor ejection mechanism of claim 1, further comprising a gear core piece extending through a central aperture of the gear such that the gear rotates about the gear core piece.

19. The test sensor ejection mechanism of claim 1, wherein the casing removably attaches to the test sensor cartridge via insertion of the foot into the opening formed in the test sensor cartridge.

20. The test sensor ejection mechanism of claim 1, wherein the moveable gear rack covers the opening formed in the test sensor cartridge when the casing is attached to the test sensor cartridge.

* * * * *